(12) United States Patent
Pacheco et al.

(10) Patent No.: US 10,617,158 B2
(45) Date of Patent: Apr. 14, 2020

(54) THERAPEUTIC FABRIC ARTICLE

(71) Applicant: CapeAble Sensory Products, LLC, Winona Lake, IN (US)

(72) Inventors: Mama G. Pacheco, Winona Lake, IN (US); Susan Hickok, Fort Wayne, IN (US)

(73) Assignee: CapeAble Sensory Products, LLC, Winona Lake, IN (US)

( * ) Notice: Subject to any disclaimer, the term of this patent is extended or adjusted under 35 U.S.C. 154(b) by 240 days.

(21) Appl. No.: 15/701,762

(22) Filed: Sep. 12, 2017

(65) Prior Publication Data
US 2018/0000171 A1   Jan. 4, 2018

Related U.S. Application Data

(63) Continuation-in-part of application No. 14/693,958, filed on Apr. 23, 2015, now abandoned.

(60) Provisional application No. 62/001,445, filed on May 21, 2014.

(51) Int. Cl.
| A47G 9/02 | (2006.01) |
| A41D 3/08 | (2006.01) |
| A41D 31/02 | (2019.01) |
| A61M 21/02 | (2006.01) |
| A41D 23/00 | (2006.01) |
| A61M 21/00 | (2006.01) |
| A61F 5/56 | (2006.01) |

(52) U.S. Cl.
CPC .............. *A41D 3/08* (2013.01); *A41D 23/00* (2013.01); *A41D 31/02* (2013.01); *A47G 9/02* (2013.01); *A47G 9/0223* (2013.01); *A61M 21/02* (2013.01); *A41D 2200/20* (2013.01); *A41D 2400/32* (2013.01); *A61F 2005/563* (2013.01); *A61M 2021/0022* (2013.01)

(58) Field of Classification Search
CPC ........................................................ A47G 9/02
USPC ..................................... 5/482, 485, 500, 502
See application file for complete search history.

(56) References Cited

U.S. PATENT DOCUMENTS

| 2,042,442 | A | | 5/1936 | Buchman |
| 4,330,982 | A | * | 5/1982 | Vissers ................. A01D 57/30 56/14.5 |
| 4,689,844 | A | * | 9/1987 | Alivizatos ............ A47C 27/086 297/452.16 |
| 4,839,934 | A | * | 6/1989 | Rojas ................... A47G 9/0207 5/485 |
| 5,606,746 | A | | 3/1997 | Shelton et al. |
| 6,383,130 | B1 | | 5/2002 | Wade et al. |
| 6,665,879 | B2 | | 12/2003 | VandenBerg |
| 7,010,814 | B2 | | 3/2006 | Benziger |
| 7,178,185 | B1 | | 2/2007 | Nattler |
| 7,870,623 | B2 | | 1/2011 | Judd |
| 2007/0028387 | A1 | | 2/2007 | Mathis |

(Continued)

*Primary Examiner* — Fredrick C Conley
(74) *Attorney, Agent, or Firm* — Taylor IP, P.C.

(57) ABSTRACT

A blanket including a first outer layer, a second outer layer and at least one linear array of weighted sections. The second outer layer is attached to the first outer layer. There is at least one channel formed between the first outer layer and the second outer layer including a first channel. The linear array of weighted sections includes a first linear array of weighted sections, and the first linear array of weighted sections is inserted into the first channel and is secured at an end of the first channel.

15 Claims, 12 Drawing Sheets

(56) References Cited

U.S. PATENT DOCUMENTS

2014/0259423 A1  9/2014  Falck

* cited by examiner

THERAPEUTIC FABRIC ARTICLE

CROSS REFERENCE TO RELATED APPLICATIONS

This is a continuation-in-part application based upon U.S. non-provisional patent application Ser. No. 14/693,958 entitled "THERAPEUTIC FABRIC ARTICLE", filed Apr. 23, 2015, which is incorporated herein by reference. Application Ser. No. 14/693,958 was based upon U.S. provisional patent application Ser. No. 62/001,445 entitled "THERAPEUTIC FABRIC ARTICLE", filed May 21, 2014.

BACKGROUND OF THE INVENTION

1. Field of the Invention

The present invention relates to a therapeutic fabric article, and, more particularly, to weighted garments and accessories therefor.

2. Description of the Related Art

The tactile system provides input to the brain for interpretation of various types of touch, pressure, temperature and pain through receptors in the skin. For example, deep pressure touch can be very calming. This type of input facilitates the release of dopamine, also known as the "pleasure chemical", in the brain that helps people maintain emotional neutrality. Dopamine activates the parasympathetic nervous system for a relaxed, neutral and balanced homeostatic state. Dopamine may neutralize cortisol and adrenaline, which contribute to the fight or flight response of the autonomic nervous system. Conversely, an excess of dopamine may increase hyperactivity, which may then be regulated by increasing serotonin levels via the proprioceptive system. Proprioception refers to the information gathered by the nervous system from one's muscles, joints, tendons and ligaments. It is also known as the "position sense", which offers a sense of grounding that is interpreted by the emotional state as perceived security and/or safety. Proprioceptive input facilitates the release of serotonin, the master regulator of the central nervous system (brain and spinal cord), as well as dopamine. Valued as the "coping chemical", serotonin breaks up dopamine thereby preventing hyperactivity and over-processing of information, resulting in a neutral state of arousal. Persons having difficulty processing information from one or both of these systems will demonstrate behaviors that impede function. Poor sensory modulation leads to a compromised body system that is interpreted by the central nervous system as being "in pieces". The brain and the body will focus on keeping the individual's self together, thereby rendering the individual substantially incapable of efficient higher cortical function. The basic sub-cortical needs must first be met before focus can be diverted to higher cortical function. Maintaining the nervous system at a calm and alert state is imperative for cognitive functions and learning.

Persons affected by impaired function of the nervous system can include those with developmental disabilities, Sensory Processing Disorders (SPD), Attention Deficit Hyperactivity Disorders (ADHD) and autism spectrum disorders. Individuals with these conditions have difficulty maintaining homeostasis within the nervous system, thereby inhibiting their ability to participate in effective learning and sometimes causing behaviors incongruent with social norms. Such identifiable behaviors can include constant movement, impulsivity, decreased attention span, inability to focus on a particular task and seeking of heavy-pressure related tasks.

Current treatments for persons affected by an impaired function of the nervous system can include pharmaceutical products, behavioral therapy, speech-language therapy, physical therapy, play-based therapy, situational therapy and nutritional therapy. Often in combination, these forms of treatment can be a tremendous benefit; yet, they are not without their own shortcomings. For instance, pharmaceuticals may elicit irresponsive results, or worse they may cause adverse side effects for a particular individual. Results from treatment in general can vary greatly from one individual to another. Therefore, partially due to the individualistic nature of conventional treatment methods, alternative additional forms of treatment were developed, including types of treatments utilizing deep pressure and tactile input therapy.

Some applications of deep pressure therapy in the prior art include use of squeeze machines, weighted blankets, and various weighted articles such as gloves or vests. These deep pressure devices have been known to release serotonin, which helps an individual feel calm and secure. However, the problem with many of these forms of deep pressure therapy is that they are restrictive and can keep the user from fully engaging in daily activities such as routine tasks, learning, common social interactions and play.

What is needed in the art is an ergonomic and discreet therapeutic garment that serves a dual sensory function with reference to the proprioception and tactile systems without sacrificing mobility and aesthetics, which thereby enables the wearer to more fully participate in daily routines and the enjoyments of life.

SUMMARY OF THE INVENTION

The present invention relates to weighted items that may be made of layers of cloth or fabric.

The present invention provides therapeutic garments and accessories therefor which are configured to serve a dual sensory function with reference to the proprioception and tactile systems, thereby increasing the wearer's functional attention and enabling the wearer to participate more fully in the activities making up his or her daily routine. The present invention is beneficial in home, school and community settings, as well as therapeutic institutional mental health settings and inpatient and outpatient medical surgery settings. The present invention is beneficial for treatments throughout the lifespan, from birth through hospice care, of persons either having neurological disabilities or being neurologically typical (NT) but demonstrating anxiety and related conditions. More specifically, the garment according to the present invention is a discreet and aesthetically pleasing intervention aimed at the neurological/sensory underpinnings contributing to unacceptable sensory-seeking behaviors in children and adults with disabilities, and neurologically typical individuals with situational anxiety.

The invention in one form is directed to a blanket including a first outer layer, a second outer layer and at least one linear array of weighted sections. The second outer layer is attached to the first outer layer. There is at least one channel formed between the first outer layer and the second outer layer including a first channel. The linear array of weighted sections includes a first linear array of weighted sections, and the first linear array of weighted sections is inserted into the first channel and is secured at an end of the first channel.

The invention in another form is directed to a layered fabric item including a first outer fabric layer, a second outer fabric layer and at least one linear array of weighted sections. The second outer fabric layer is attached to the first outer fabric layer. There is at least one channel formed between the first outer fabric layer and the second outer fabric layer including a first channel. The linear array of weighted sections includes a first linear array of weighted sections, and the first linear array of weighted sections is inserted into the first channel and is secured at an end of the first channel.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 1:
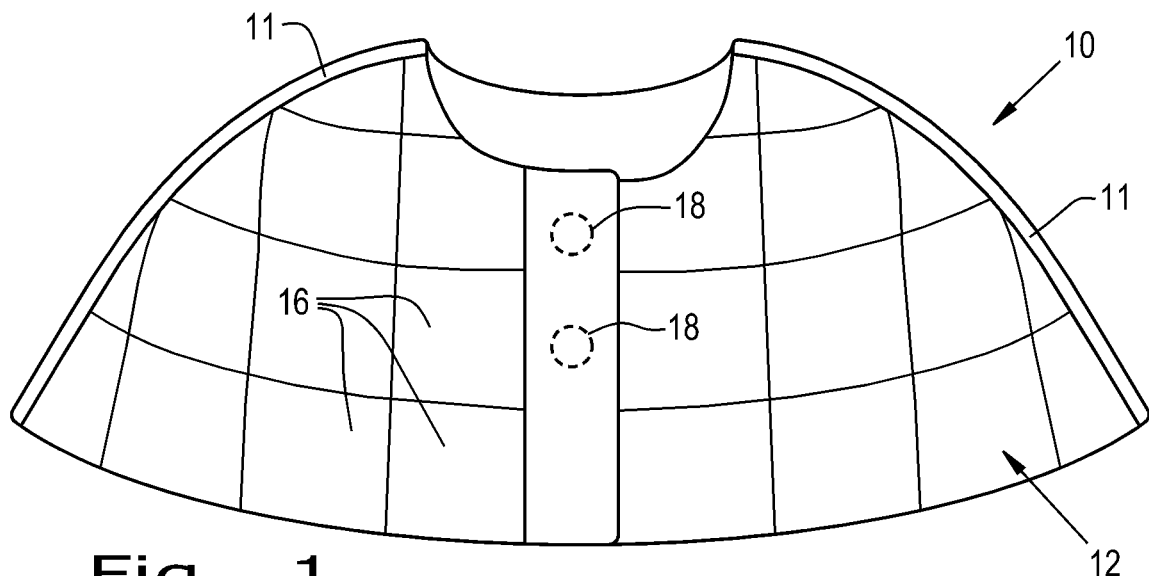
FIG. 1 is a front view of an embodiment of the inventive garment.
Figure 2:
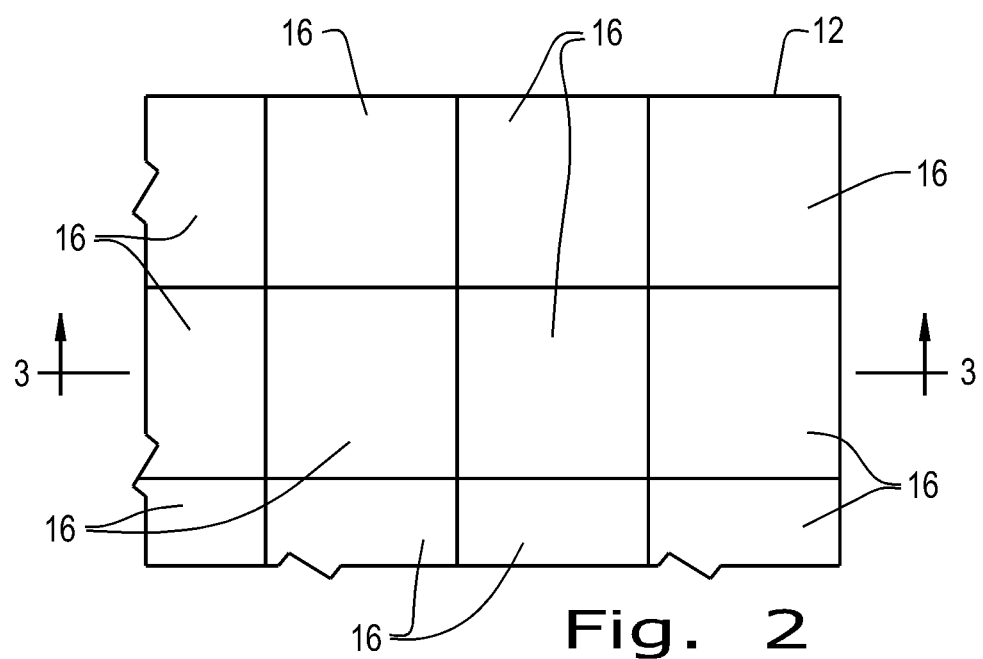
FIG. 2 is a diagram that illustrates the fabric pattern of the inventive garment.
Figure 3:
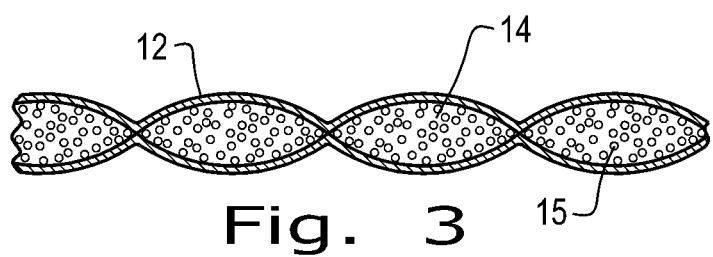
FIG. 3 is a diagram that illustrates the distribution of a weighted material inside the fabric shell of the inventive garment.

Referring now to the drawings, and more particularly to FIGS. 1-3, there is shown an embodiment of the inventive garment 10, which is generally constructed of a fabric shell 12 that has a quilted pattern in the form of a plurality of quilted squares 16 for securing a weighted filling 14 therein. The garment 10 further includes a pair of curved shoulder panels 11 and at least one fastener 18.

The garment 10 is generally configured such that there is a substantially even weight distribution within the quilted squares 16 from an anterior side, shown in FIG. 1, to a posterior side (not shown) of the garment 10. According to the embodiment shown in FIG. 1, the garment 10 encompasses the shoulder girdles of a wearer, and it has a contour in the likeness of a shoulder cape. The curved shoulder panels 11 allow a clear, defined fit, which in combination with the elastic character of the fabric shell 12 maintains the placement of the garment 10 without inhibiting functional upper-body use of the wearer. Additionally, due to the snug fit of the garment 10 around the shoulder girdle, there is a greater surface contact area for sensory input. This design ensures accurate and consistent pressure to the body via the peripheral nervous system. This even weight distribution provides necessary input to the surface area of the mid chest region, shoulder girdle (both anterior and posterior) and upper back region. Further, the dermatomes are activated with constant and repeated stimulus each time the garment is applied or worn while providing the user with a secure fit that provides a "hugging" or compression fit of comfort.

Fabric shell 12 of the present embodiment is a plush material with a slight elasticity, which adds both to the tactile and proprioceptive benefit of the garment 10, while providing a comfortable compression fit. The fabric shell 12 houses the weighted filling 14, which can be in the form of a glass or polymer pellet filling 15 as in the present embodiment, or in the form of any other suitable filling that is durable and washable. The fabric shell 12 of the present embodiment has a quilted pattern in the form of a plurality of quilted squares 16. However, the fabric shell 12 may have any geometric pattern that equally distributes the weighted filling 14 throughout the garment 10, including a quilted triangular pattern or a diamond pattern. Each quilted square 16 is designed to be substantially the same size and to contain substantially the same amount of the weighted filling 14. In the embodiment shown in FIG. 1, each quilted square 16 is 2½ square inches; however, the size of each quilted square 16 is not limited to 2 ½square inches. The quilted squares 16 could be sized in a range from 1 to 3 square inches. Further, the quilted geometric pattern may be comprised of various shapes that are not of equal size.

The fastener 18 is positioned at the anterior side of the garment 10 such that the wearer can easily don and doff the garment 10. The embodiment shown in FIG. 1 has a fastener 18 in the form of two magnetic fasteners (not shown). Additional possible fasteners include buttons, snaps, clasps, laces, Velcro® or any other suitable fastener for securing the garment about the body of the user. Magnetic fasteners provide simplicity in fastening and they eliminate the potential for startling the wearer due to a sudden auditory stimulus, as would snaps or hook and loop fasteners. Additionally, magnetic fasteners allow for the garment 10 to be readily reversible. The magnetic fasteners are housed within the fabric shell 12, in other words they are sewn into the interior of the garment 10, and they do not extend to the exterior of the garment 10. Therefore, the wearer's temptation to fidget with the fastener 18 in the present embodiment is reduced, allowing the wearer to more easily focus on the task at hand.

Figure 4:
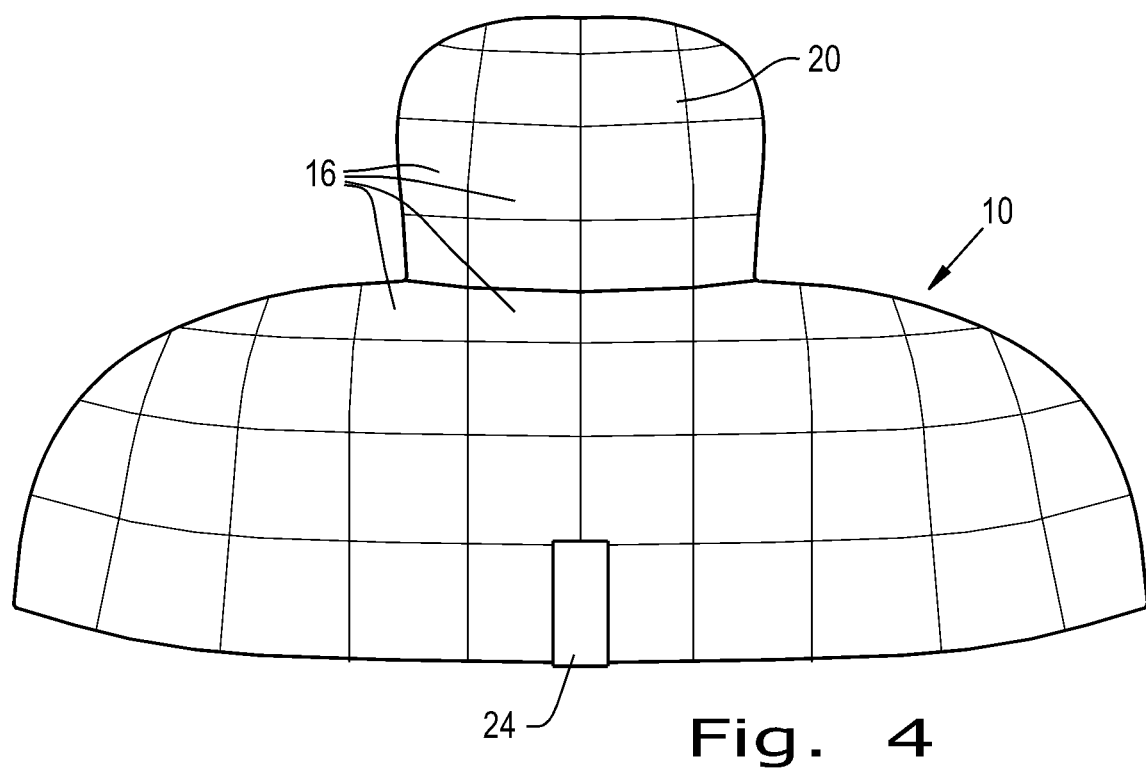
FIG. 4 is a posterior view that illustrates an integrated hood attached to the embodiment shown in FIG. 1.

Referring now to FIG. 4, the garment 10 may further include an integrated hood 20, which also is constructed of the same plush fabric shell 12 shown in FIG. 3. The integrated hood 20 includes the weighted filling 14, which is substantially evenly distributed throughout the fabric shell 12 of the hood 20. The integrated hood 20 provides an additional dimension of sensory input, while maintaining the quilted configuration and cohesive appearance. It is also feasible for the integrated hood 20 to be formed as a separate unit, which can be coupled with the garment 10 by using an additional fastener or a set of additional fasteners (not shown). The additional fasteners may be in the form of magnetics, buttons, snaps, clasps, Velcro® or any other fastener capable of securing the garment 10 to the hood 20.

Additionally, as illustrated in FIG. 4, a loop 24 may be provided on the posterior, bottom edge of the garment. This facilitates a greater sense of independence because when the integrated hood 20 is not in use the wearer can easily hang it in his or her "cubby", locker at school, or on a hook in a social atmosphere or at home.

Figure 5:
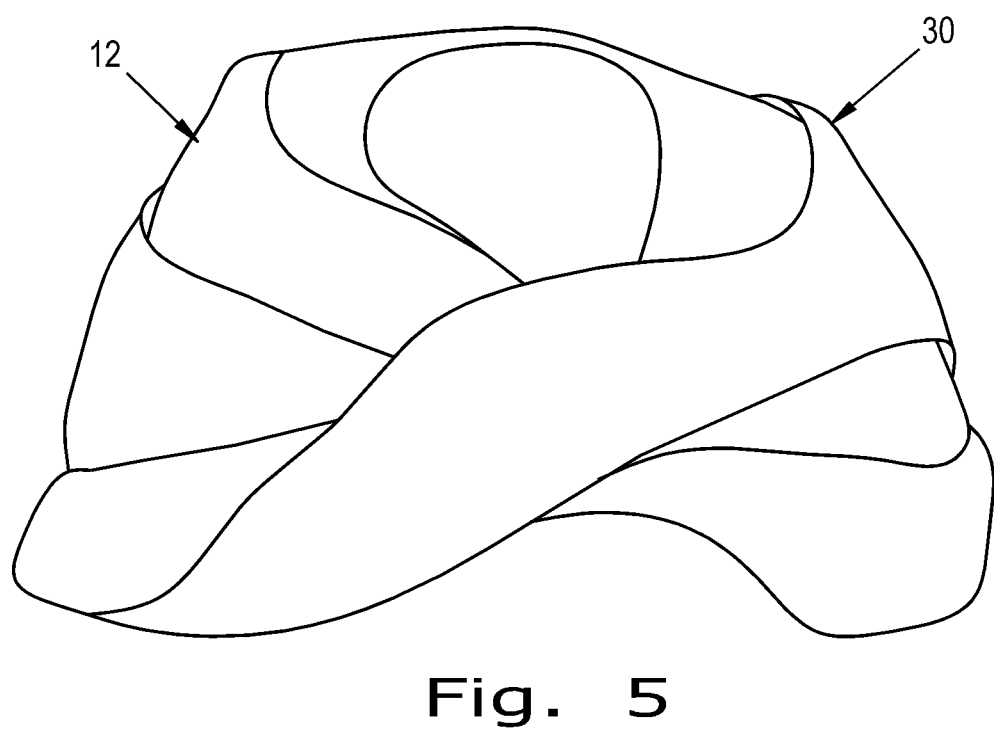
FIG. 5 is a front view of a second embodiment of the inventive garment, which is in the form of an endless loop of fabric.

Referring now to FIG. 5, there is shown a second embodiment of the inventive garment 10 according to the present invention in the form of an endless loop of fabric 30, which may be draped about the head, shoulders and neck of the wearer. Garment 30 includes the fabric shell 12, shown in FIG. 3, which is constructed with a plurality of quilted squares 16, as illustrated in FIG. 2. The quilted squares 16 include a weighted filling 14, which can be in the form of a plurality of glass or polymer pellets (not shown) therein. According to this second embodiment of the present invention, the weight of the weighted material 14 is distributed substantially evenly across the entirety of the garment 30.

Figure 6:
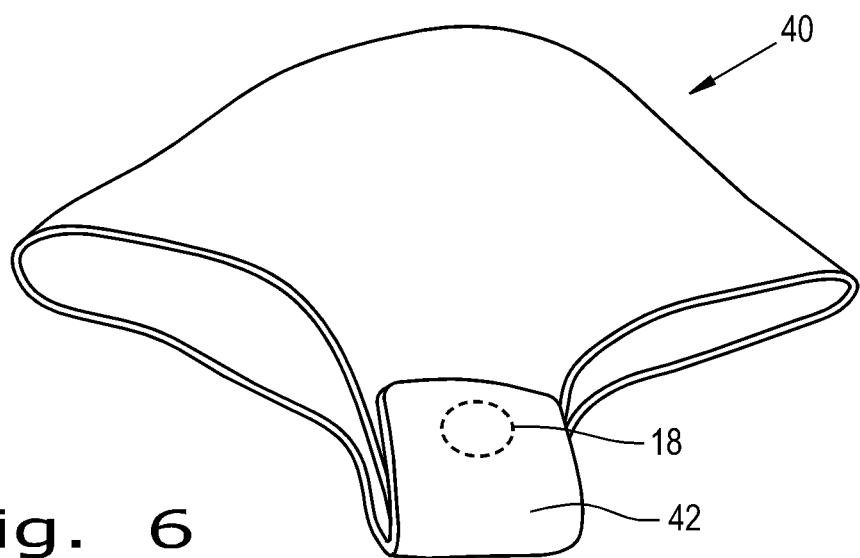
FIG. 6 is a side perspective view that illustrates a third embodiment of the inventive garment in the form of a stand-alone hood.

Referring now to FIG. 6, a third embodiment of the inventive garment is provided in the form of a stand-alone hood 40. The hood 40 includes a chinstrap 42 and at least one fastener 18. Hood 40 provides proprioceptive input at the crown of the head of a user, via even disbursement of weight to the frontal and parietal portions of the cranium. The chinstrap 42 is configured for applying a predetermined amount of pressure to the temporomandibular joint (TMJ) when the chinstrap 42 is fastened under the chin of a user. The TMJ is a site for sensory stimulation and organization. A pressure input by the chinstrap 42 advantageously reduces the quantity and intensity of maladaptive oral habits, for example, excessive mouthing, teeth grinding and chewing on clothing and/or fingers. The fastener 18 can include magnets, buttons, snaps, clasps, laces, Velcro® or any other suitable fastener for securing the chinstrap 42. Exemplary uses for the stand-alone hood 40 may include: (1) Use in transition prior to getting a child's hair cut; (2) Calming an otherwise over-stimulated child in a loud, bright community setting, such as a grocery store, department store or restaurant; (3) Minimizing environmental input (i.e., light, noise and movement of peers) from the classroom in a school setting; and (4) Calming an overwhelmed child in a social setting with a number of different people and activities going on around the user.

Figure 7:
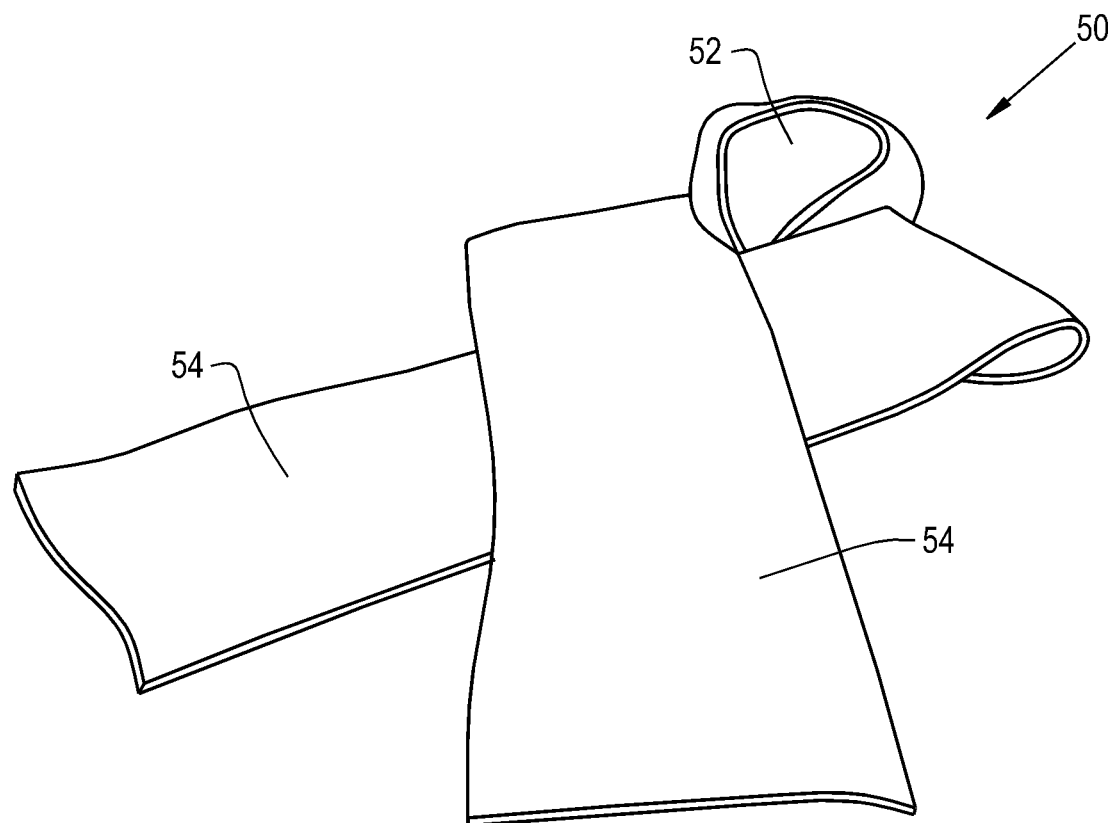
FIG. 7 is a perspective view that illustrates a fourth embodiment of the inventive garment in the form of a hooded wrap garment.

Referring now to FIG. 7, there is shown a fourth embodiment of the present invention in the form of a hooded wrap garment 50, constructed of the same fabric shell 12 described above and having an even distribution of the weighted filling 14. The weighted filling 14 can be, for example, a glass or polymer pellet filling (not shown) encapsulated within the fabric shell 12 for even weight distribution across the area of the garment 50. The garment 50 further includes a hood portion 52 and a pair of symmetrical, elongate structural members 54 that extend outwardly from the hood portion 52. The extended length of the elongate structural members 54 provides additional versatility in how the hooded warp garment 50 is worn because the elongate structural members 54 can be extended up to 4 or more feet (ft.). For example, depending upon the input desired, the length of the hooded wrap garment 50 may be wrapped or draped unilaterally or bilaterally over the shoulders of the user, or may be draped comfortably on the lap or about the waist of the wearer when in a seated or reclining position. Upon standing, the hooded wrap garment 50 is configured to drape downwardly to the top of the knees of a wearer, thereby eliciting a greater pressure input through the shoulders as is promoted by gravitational effects. Advantageously, the hooded wrap garment 50 provides flexibility in use and directed input to the proprioceptive and tactile sensory systems.

The hooded wrap garment 50 according to the present invention may also be configured without the hood portion as a simple wrap or scarf (not shown). Such a wrap or scarf can be wrapped over one or both shoulders, or it may be draped about the neck of the user to extend down the back or the front of the body. Reverse wear of such a wrap or scarf, in other words with opposing ends extending down the back of the wearer, would elicit a calming sense due to the selected proprioceptive and tactile input on the user's nervous system via providing substantially uniform weight distribution across the chest and the sternum.

Figure 8:
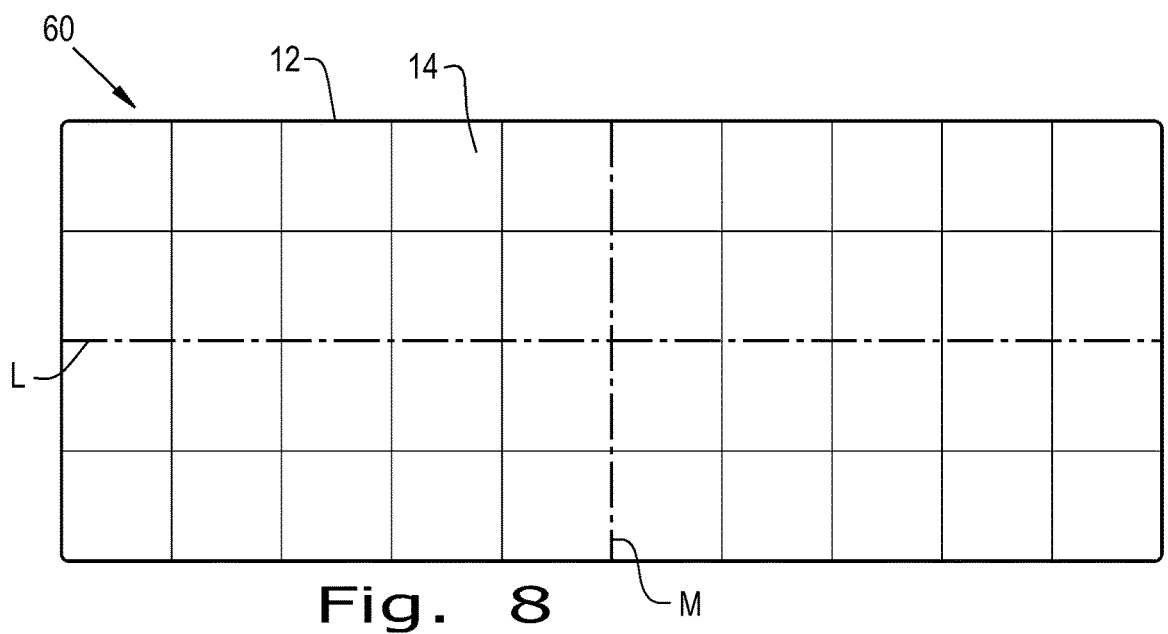
FIG. 8 illustrates a fifth embodiment of the present invention in the form of a lap pad.

Referring now to FIG. 8, there is shown a fifth embodiment of the present invention configured as a lap pad 60. The lap pad 60 is formed of the same plush, quilted fabric shell 12 with the weighted filling 14 therein, which is substantially evenly distributed across the area of the lap pad 60 for maximum proprioceptive input. The lap pad 60 may be used simply as a weighted lap pad or folded in half to increase the weight distribution over a smaller area, for example, at the center of the lap of a user. Additionally or alternatively, the lap pad 60 may be utilized as a muff when a user's hands are placed between the layers of the folded lap pad 60, offering additional proprioceptive and tactile input to the hands, thereby calming the user. Also, by positioning the hands of a user within the folds of the lap pad 60, the upper extremity tremoring of a user may be dampened, thereby soothing the user through the enhanced proprioceptive and tactile inputs on the nervous system.

Optionally, a plurality of magnetic fasteners (not shown) may be provided at the corners of the lap pad 60, affixed within the fabric shell 12. This would allow the user to secure the lap pad 60 along a longitudinal axis L or a lateral axis M for increased versatility in use, as shown in FIG. 8. For example, the lap pad 60 may be secured around the neck of a user for targeted proprioceptive and tactile input to the neck and/or shoulders for a more proximal proprioceptive experience. Alternatively, the lap pad 60 may be worn around the hips as a belt for proximal stability and input at the pelvic girdle. This is particularly advantageous for providing body-awareness for ambulation and gait training.

Figure 9:
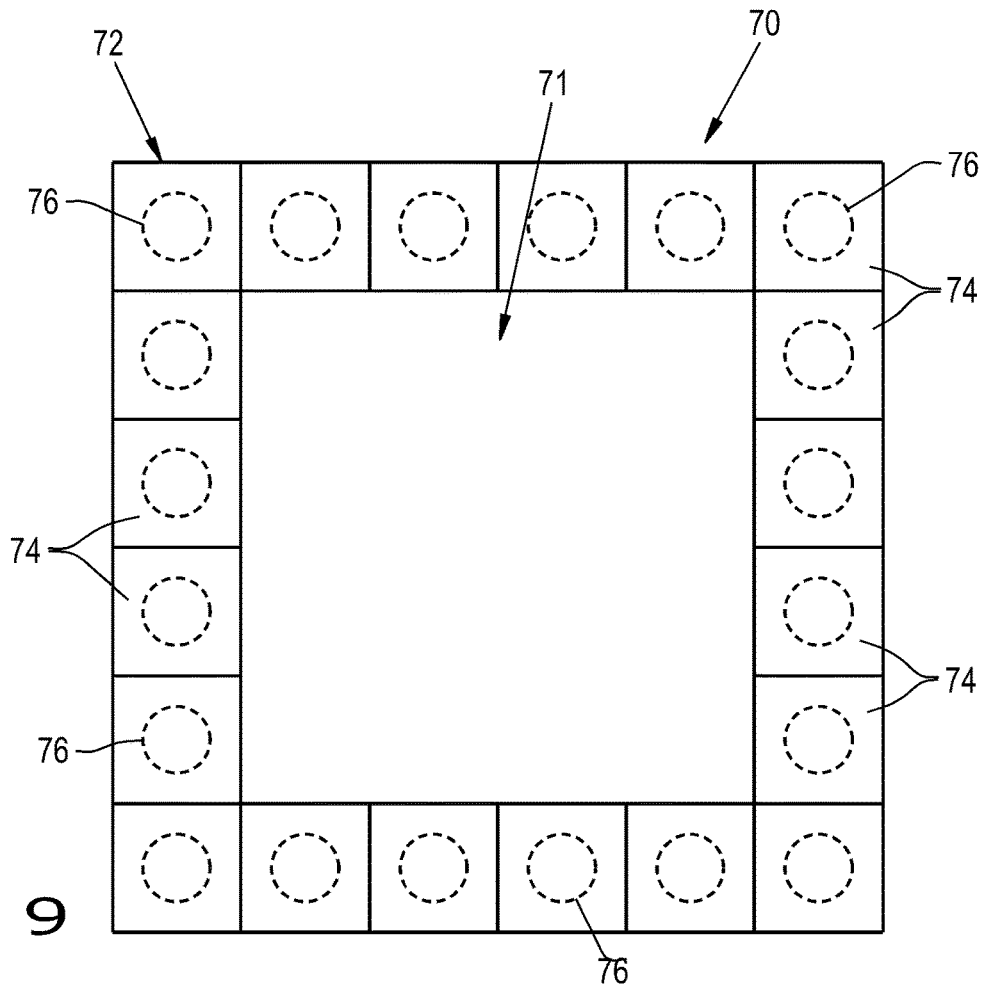
FIG. 9 is a diagram that illustrates a sixth embodiment of the inventive garment in the form of a perimeter blanket.

Referring now to FIG. 9, a sixth embodiment of the present invention provides a perimeter blanket 70, which includes a central panel 71 and a perimeter area 72 formed by the fabric shell 12, which is illustrated in FIG. 3. The perimeter area 72 further includes a plurality of quilted squares 74 that house the weighted filling 14, which is substantially uniformly distributed throughout the fabric shell 12. Perimeter area 72 outlines the central panel 71, which is also formed of the same plush fabric as perimeter area 72, for a calming input into the tactile sensory system. Advantageously, since the quilted squares 74 are positioned about the perimeter it allows the user to selectively distribute the weight to provide a desired amount of pressure and tension across selected areas of the body, thereby allowing the user to define the desired proprioceptive input into the nervous system. The perimeter blanket 70 thereby provides both weight and compression when draped and/or wrapped about the body with varying degrees of tension. Further, because of the unique design and weight distribution, the perimeter blanket 70 will not shift off of a user's lap or body, despite active movement.

The perimeter blanket 70 may further optionally include, encased within the fabric shell 12, a plurality of magnetic inserts 76 having respective alternating polarities positioned around the periphery of the perimeter blanket 70 such it may be gathered up into a sack or a bag for a variety of uses.

Figure 10:
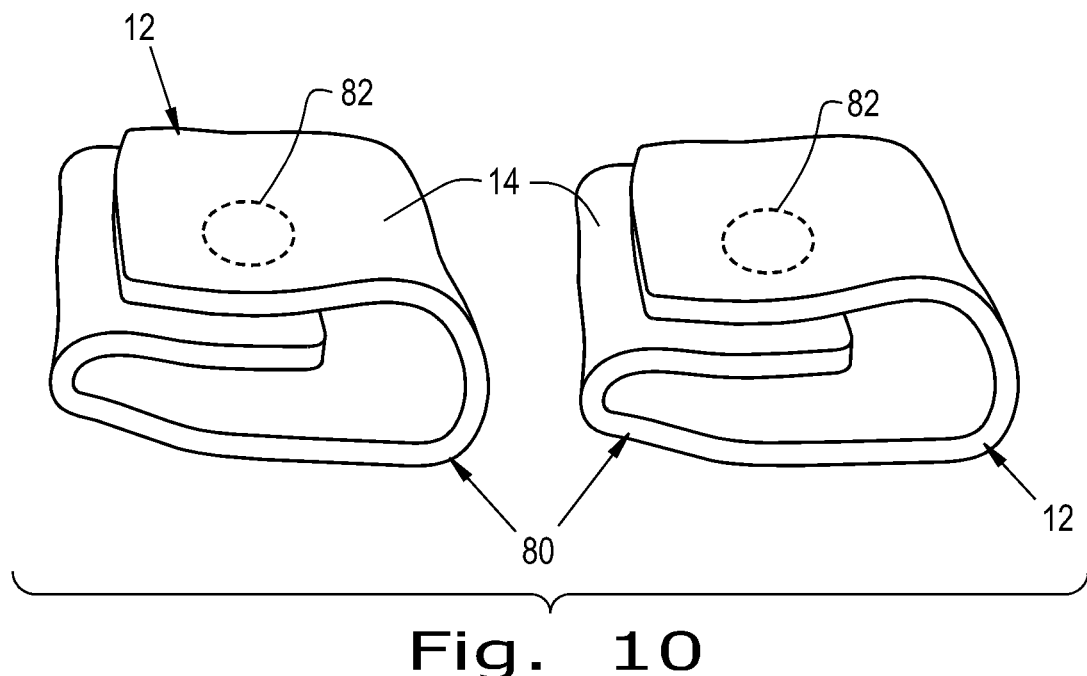
FIG. 10 is a perspective view that illustrates a seventh embodiment of the inventive garment in the form of proprioceptive and tactile input bands.

Referring now to FIG. 10, there is shown a seventh embodiment in the form of proprioceptive and tactile input bands 80, which may be positioned about the wrists or ankles of a user. The bands 80 include the plush fabric shell 12, the weighted filling 14 and a fastener configured as a plurality of magnets 82. Provided in varying widths and lengths, the bands 80 offer proprioceptive input for a number of functional activities, for example, handwriting and fine-motor activities when positioned about the wrists. The magnets 82 are hidden within the fabric shell 12 and are positioned at opposing ends within contiguous quilted squares (not shown), such that bands 80 may be folded lengthwise for a greater intensity of weight distribution. The plush fabric shell 12 has a slight elasticity that offers an additional sensory component of compression, depending upon the tension applied to bands 80 in positioning them about the body.

Figure 11:
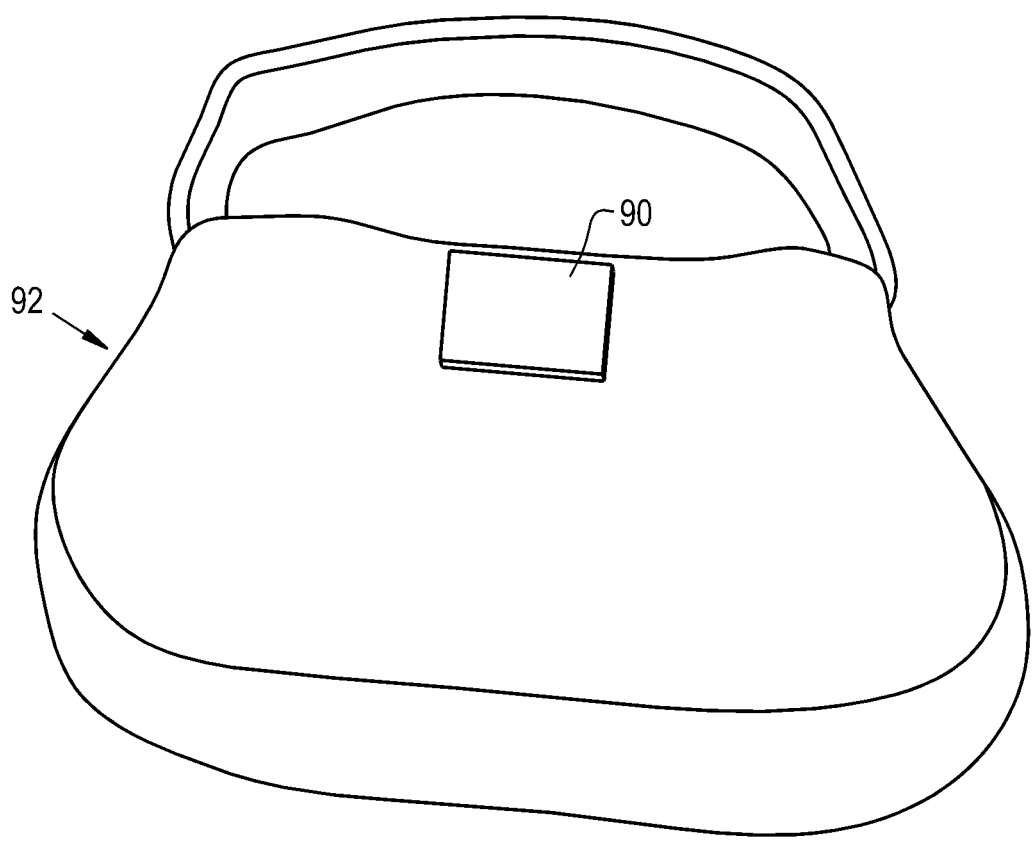
FIG. 11 illustrates an additional accessory of the present invention in the form of a normalized and fashionable purse.

According to the present invention, additional optional accessories may be utilized in association with any of the above-referenced embodiments of the present invention. For example, magnetic patches 90 (see FIG. 11) may be secured to any of the above-identified embodiments using a fastener 18. Such magnetic patches 90 may be used to provide visual or tangible recognition of tasks accomplished throughout the user's day. These tasks may include visual presentations of information such as emotional status, functional prompts for visual sequencing, self-help and/or daily skills and routines, sports, therapy sessions, etc.

Also, an additional accessory in the form of a purse 92 (see FIG. 11), bag or backpack (not shown) may be provided in a matching fabric pattern to be utilized in association with the above-identified inventive garments, thereby providing an aesthetically pleasing, socially acceptable or normalized and fashionable set, while also meeting the specialized neurologic needs of the user. Selective weighting of the purse 92, bag or backpack may be provided such that the fashionable accessory can be converted for purposes of selective proprioceptive input at predetermined points across and around the user's body. The purse 92, bag or backpack may also be provided with overlapping magnets (not shown) on the straps to offer a safety release feature.

Figure 12:
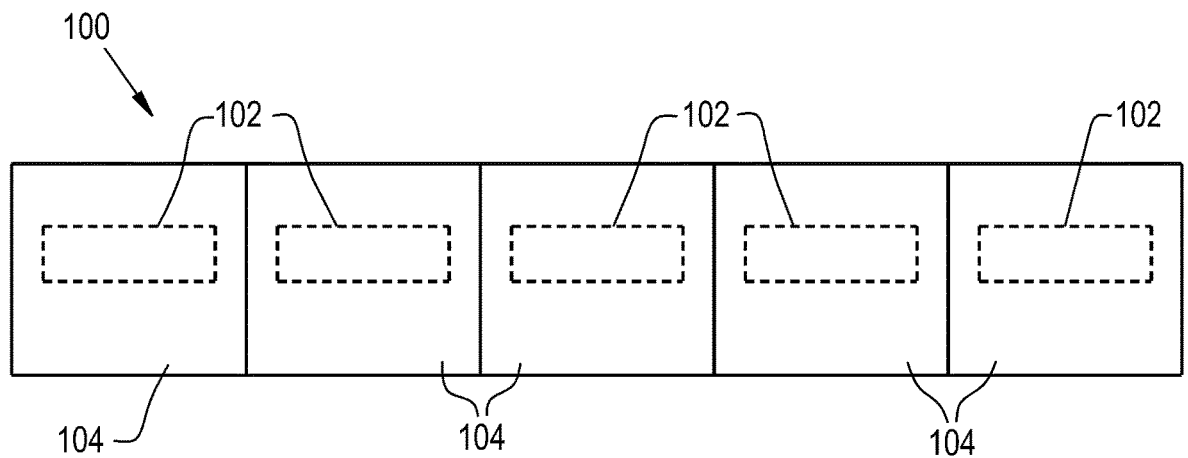
FIG. 12 is a diagram that illustrates another additional accessory of the present invention in the form of a therapeutic fidget.

Referring to FIG. 12, another accessory is shown as an inventive therapeutic fidget 100. The fidget 100 includes a plurality of square linear magnets 102 positioned within a plurality of quilted fabric squares 104, which aid in self-regulation of a user to calm and organize the nervous system. By actively grasping and pulling the magnetic strips 102 apart, tensile qualities of the fidget 100 engage receptors of the nervous system and thereby provide the desired proprioceptive, auditory and tactile inputs. Likewise, the alternating alignment of the magnets 102 piques the interest of the user by experiencing proprioceptive input via the "repelling/oppositional" forces. As can be seen in FIG. 12 each of the fabric squares 104 are coupled to at least one other fabric square 104, each having magnets 102 centrally located within fabric squares 104. Each magnet 102 has a corresponding shape with the other magnets 102. FIG. 12 also illustrates that the fabric squares 104 form a linear array of fabric squares, with each of the fabric squares 104 have no more than two other fabric squares 104 adjacent thereto.

Figure 13:
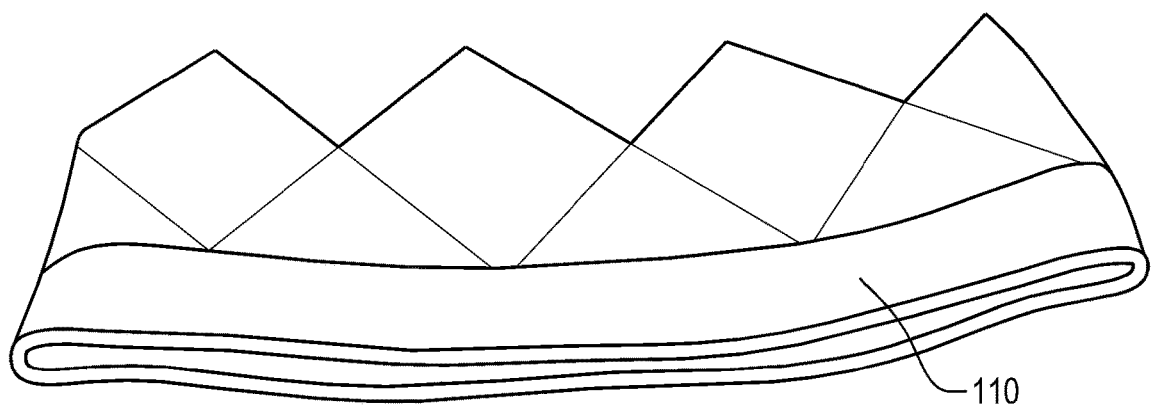
FIG. 13 is a perspective view that illustrates an optional additional accessory of the present invention of in the form of a crown headband.

Also along these lines, FIG. 13 illustrates another inventive accessory in the configuration of a crown headband 110. The crown headband 110 provides selective pressure at a plurality of points around the head, giving the wearer a fitted, compression-like feel. Circumferential input to the area just above the supra-orbital processes provides direct neurological benefits. These benefits can include activation of the body's Labyrinthine righting reflex and proprioceptive balancing. With such neuromuscular re-education, postural alignment can be obtained via activation of the spinal nerves, enhancing the body's capacity for higher cortical learning.

In addition, according to the present invention, there is provided a magnetic book (not shown) that includes a plurality of magnets positioned at a perimeter of a plurality of pages to provide positive intensity resistance, while fostering literacy and functional communication skills. The magnetic book of the present invention may be utilized to provide the user with visual clues to allow the user to participate in their day with greater independence. Visual supports are graphic clues that can be used to aid communication between the caregiver and the patient or user of the book. The inventive magnetic book may also be used as an environmental prompt that aids a child in remembering what is expected of them in a certain activity or routine. The invention may be modified to meet the needs of (1) Social stories in the form of a personalized reference to daily routines and activities, providing comfort and assistance in memory and self-regulation; (2) Visual schedules by laying out the events of a day or routine, one-by-one, and by giving a clear sense of the sequence and expectations of the day; (3) First-Then Boards which show the sequence of events and teach that in order to get a reward the child or patient must sometimes perform a less favorable activity first; and (4) Choice Boards which provide different options of what a child would like to do within activities and routines, thereby helping a user to focus on appropriate options and efficient communication of desires.

Figure 14:
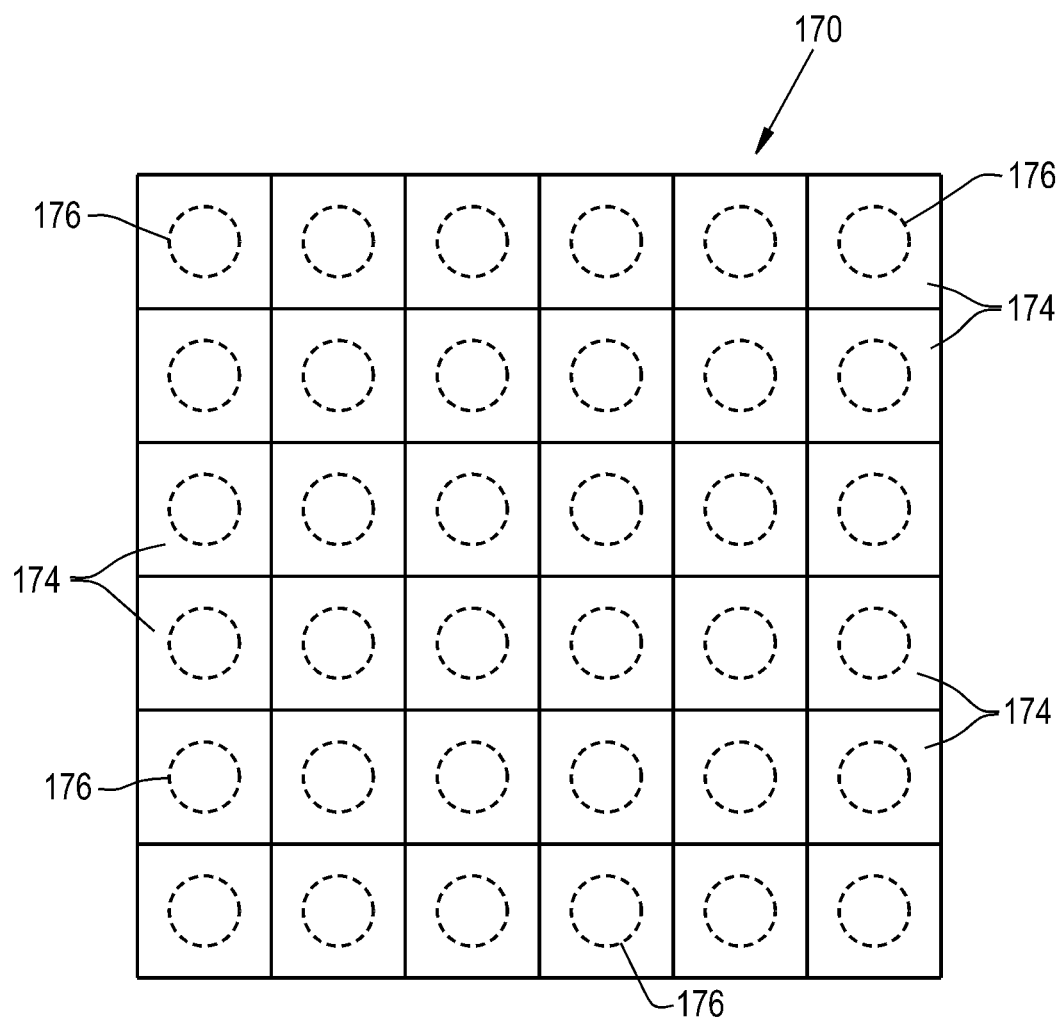
FIG. 14 is a view of another embodiment of a fidget introduced in FIG. 12.

Now, additionally referring to FIG. 14, there is shown another embodiment of the present invention in the form of a weighted blanket 170 that is similar to perimeter blanket 70, but having a complete array of quilted squares 174 each having weighted fillings 176 therein. The weighted fillings 174 are substantially uniformly distributed throughout the fabric shell. Advantageously, since the quilted squares 174 are positioned in the form of an array it allows the user to selectively distribute the weight to provide a desired amount of pressure and tension across selected areas of the body, thereby allowing the user to define the desired proprioceptive input into the nervous system. Blanket 170 provides both weight and compression when draped and/or wrapped about the body with varying degrees of tension. Blanket 170 may further optionally include, encased within the fabric shell, a plurality of magnetic inserts 176 having respective alternating polarities positioned around the periphery of blanket 170 such it may be gathered up into a sack or a bag for a variety of uses.

Figure 15:
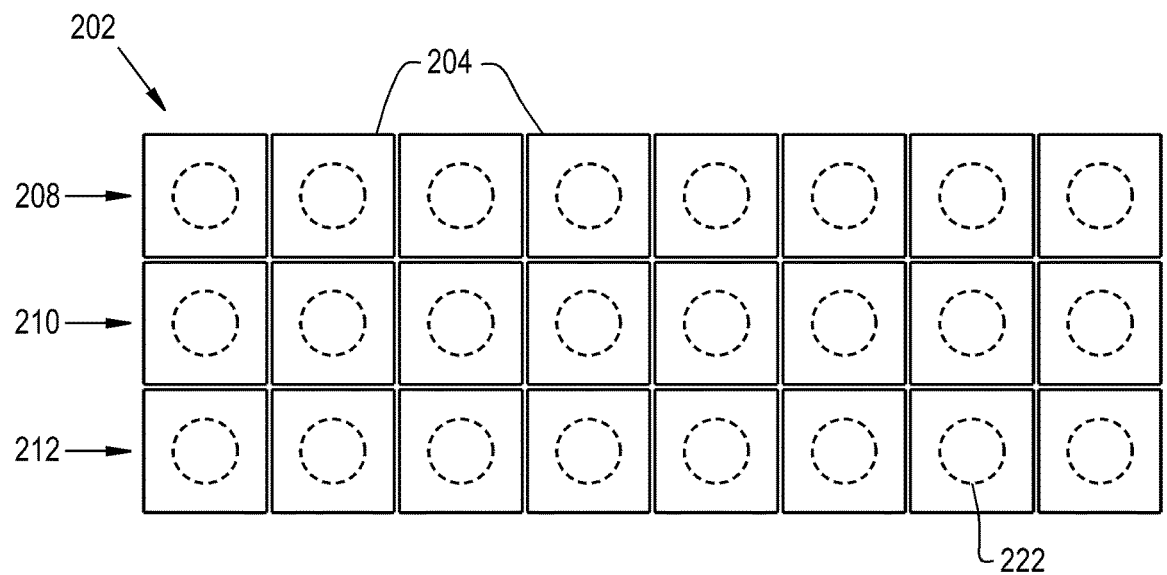
FIG. 15 is a view of an array of elements included in the fidget of FIG. 14.
Figure 16:
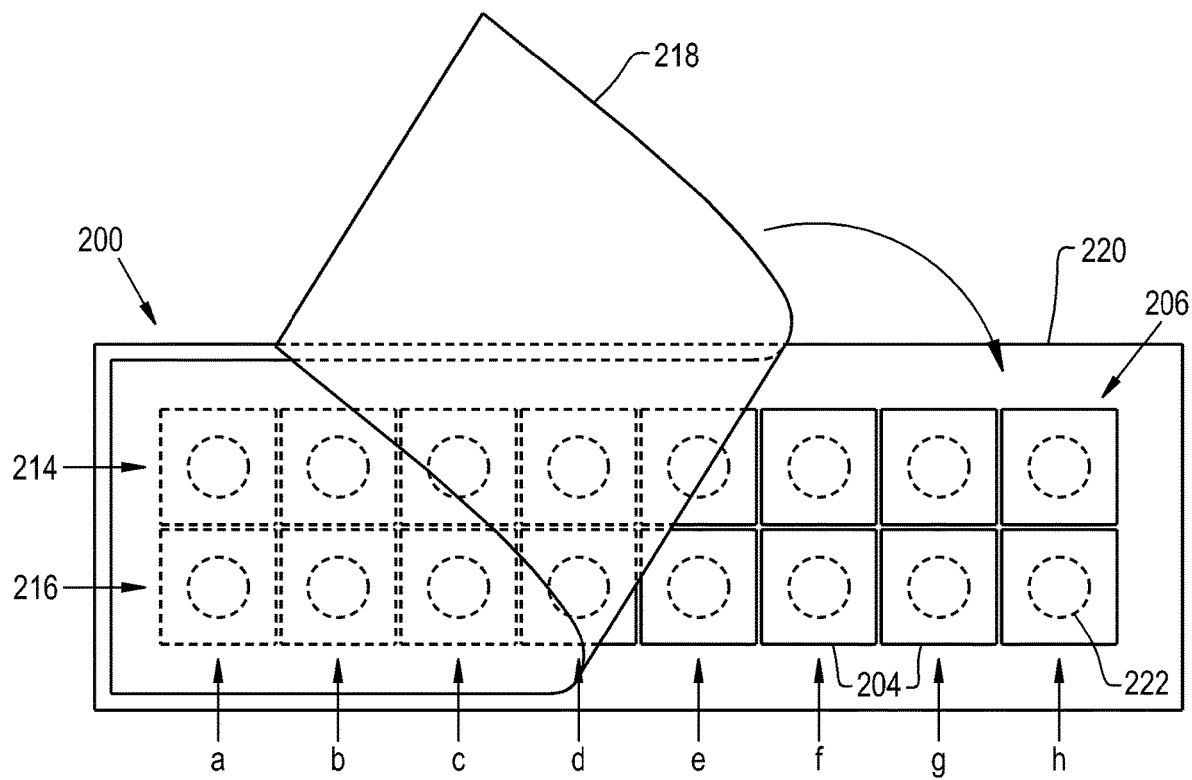
FIG. 16 illustrates a step in the forming of a fidget based on an array of elements, illustrated in FIGS. 14 and 15.

Now, additionally referring to FIGS. 15 and 16 there are shown other variants of the present invention in the form of a layered fabric item 200, where an array 202, of twenty-four filled elements 204, which can include substantially equal amounts of glass or polymer pellets, are shown in FIG. 15 and an array 206 of sixteen filled elements 204 are shown in FIG. 16. Considering the arrangement of FIG. 15, array 202 can be considered to have three linear arrays 208, 210 and 212, each with eight elements 204. In a similar fashion, fabric item 200 can have two linear arrays 214 and 216 that are arranged in array 206. Here fabric item 200 has two outer fabric layers 218 and 220 that are used to enclose array 206. While it is contemplated that elements 204 can be arranged as individual elements that are then positioned and individually secured to fabric layers 218 and 220, it is also considered that linear arrays of elements 204 are manufactured and arranged side-by-side and attached to fabric layers 218 and 220 to form a finished fabric item 200. Fabric layers 218 and 220 are secured to each other and may be secured through array 206 to form a quilted appearance. It is also contemplated that selected seams may be used to secure linear arrays 214 and 216 to layers 218 and 220.

Each filled element 204 can have a weighted filling 222 therein or item 222 can be magnets 222 having magnetic polarities that are arranged for specific purposes. For example, in fabric item 200 (which can also be called a fidget 200), each magnet 222 in linear array 214 can be arranged to have the same or opposing polarities as the immediately adjacent magnet 222. For purposes of explanation each element in linear arrays 214 and 216 are assigned positions a-h therein, and will be referred to as magnet 214a through 216h, and the polarities will be referred to as North (N) facing out of the page or South (S) facing out of the page. One conceived pattern is for magnet 214a to be N and magnet 214b to be S and this alternating pattern continues along linear array 214; and that magnets 216a-h be arranged in a contra pattern of S-N-S-N-S-N-S-N. In this pattern each magnet 222 will be an opposite polarity to its adjacent neighbor. With this arrangement fidget 200 can be folded along the numerous intersections between elements 204 in various ways with the attractive magnetic forces arranging a centering and coupling of each fold. The fidget 200 presents a therapeutic interest for the user, to arrange, rearrange and flip the fidget around to investigate the various ways that it can be arranged, providing physical therapeutic possibilities for the hands, eye-hand coordination exercises and interest to occupy the mind.

Figure 17:
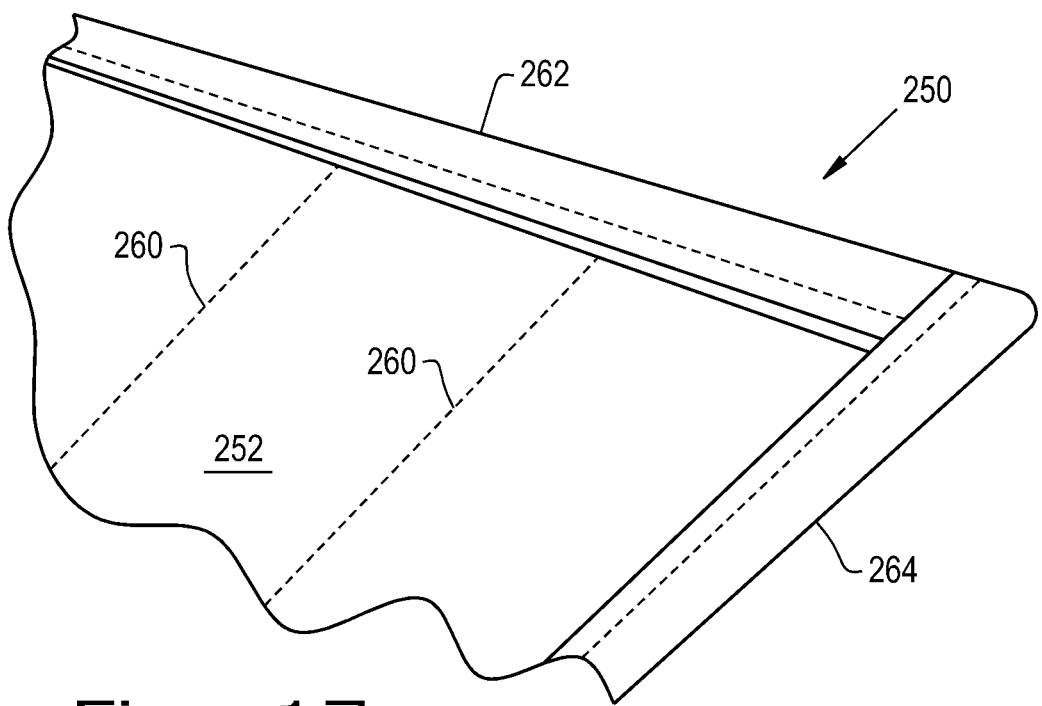
FIG. 17 is a perspective view of an embodiment of the present invention illustrated as a folded blanket having weighted arrays of elements therein.
Figure 18:
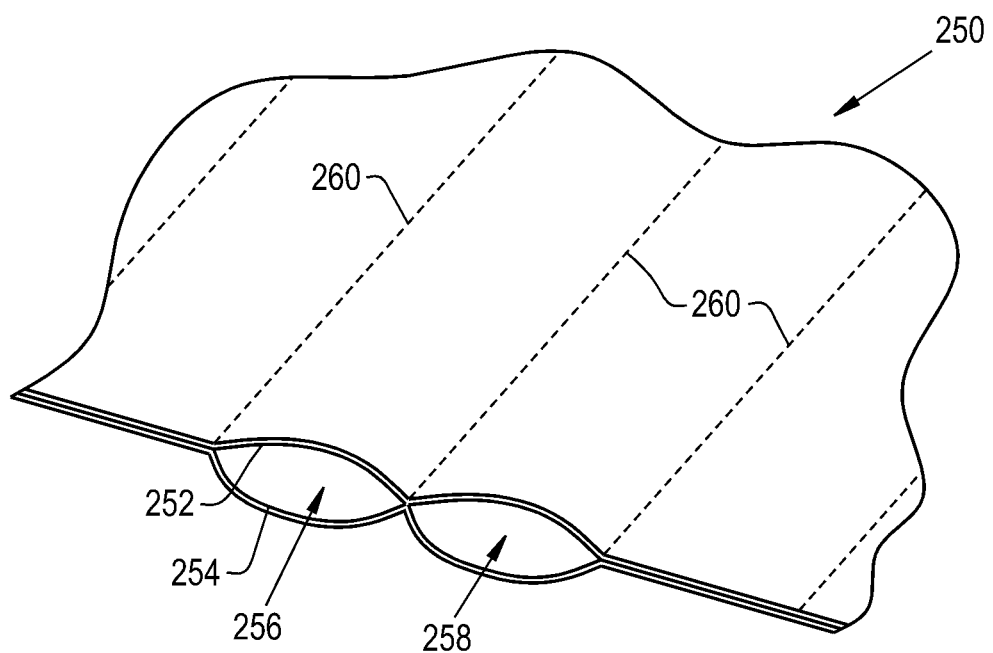
FIG. 18 illustrates open channels in the blanket of FIG. 17.

Now, additionally referring to FIGS. 17 and 18, there is shown yet another embodiment of the present invention in the form of a blanket 250 having outer fabric layers 252 and 254 that are arranged to have channels 256 and 258 formed therein by seams 260 that proceed along a length of blanket 250 with an end seamed piece 262 and a side seamed piece 264 finishing the look of blanket 250. While, for purposes of illustration, two channels 256 and 258 are shown, there are channels all along the width of blanket 250.

Figure 19:
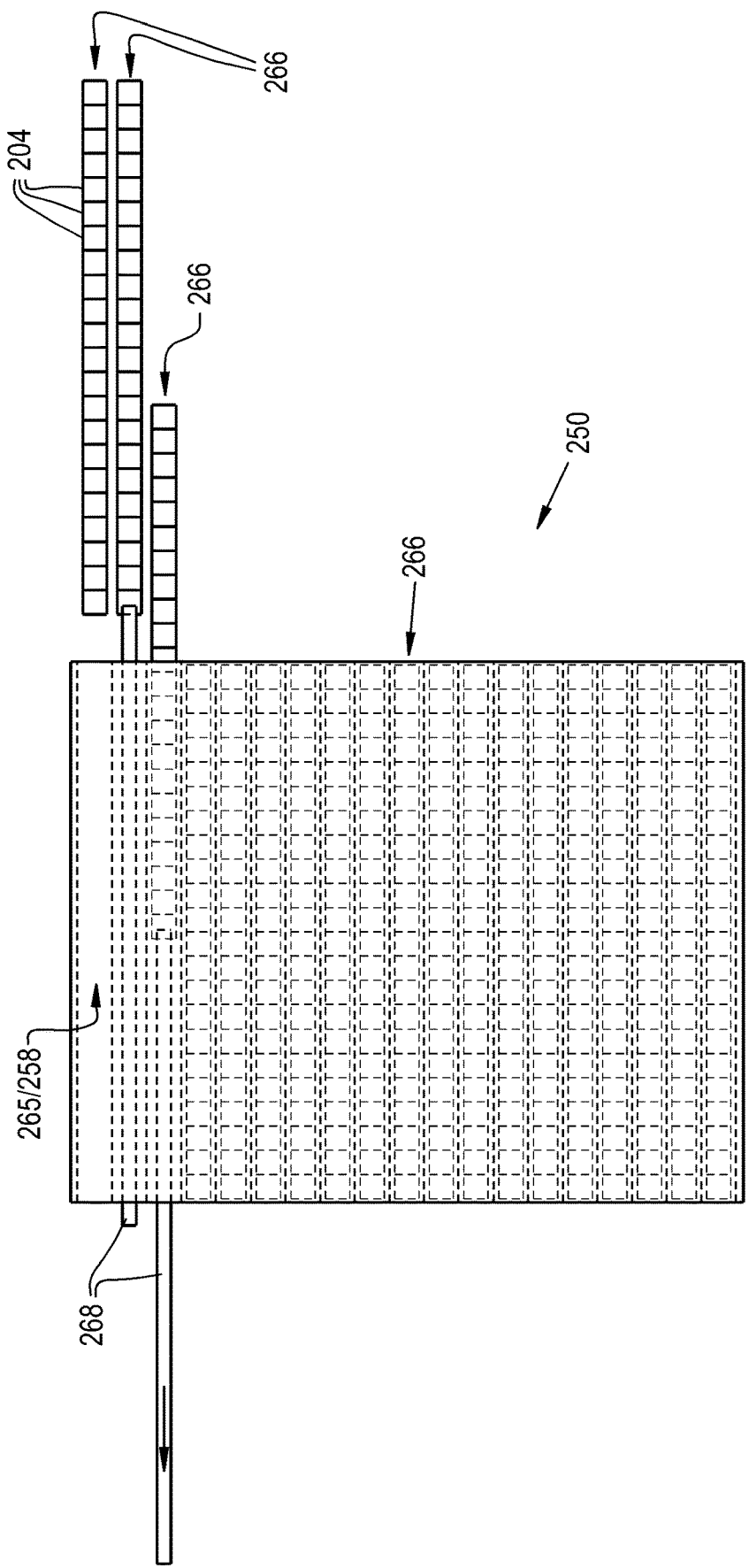
FIG. 19 illustrates the insertion of the weighted arrays of the present invention being inserted into the open channels of the blanket illustrated in FIG. 18.
Figure 20:
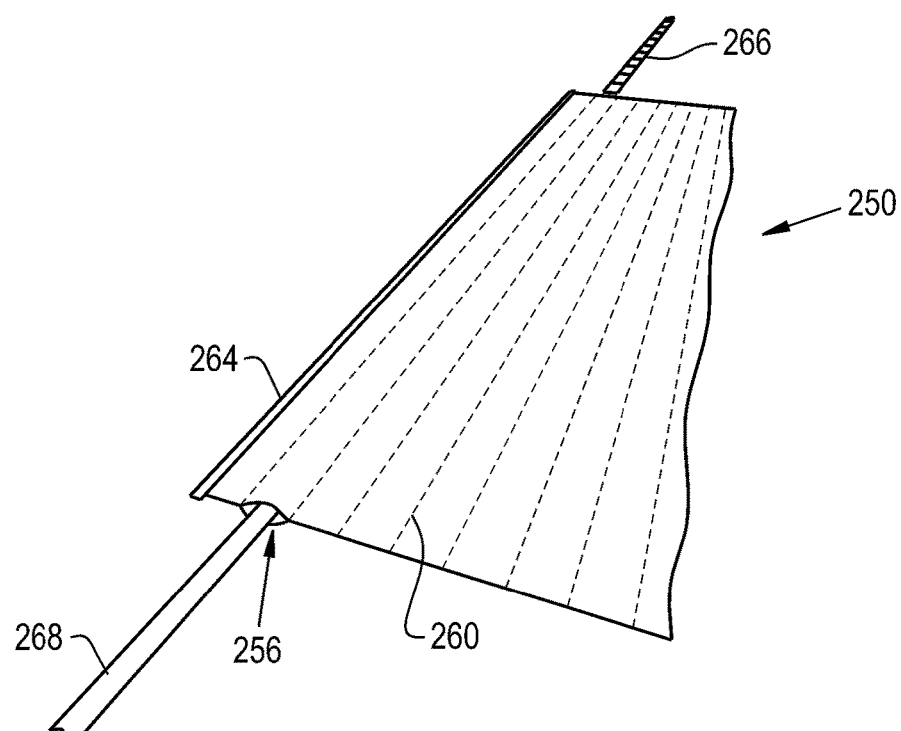
FIG. 20 illustrates the pulling of an array into an open channel of the blanket.
Figure 21:
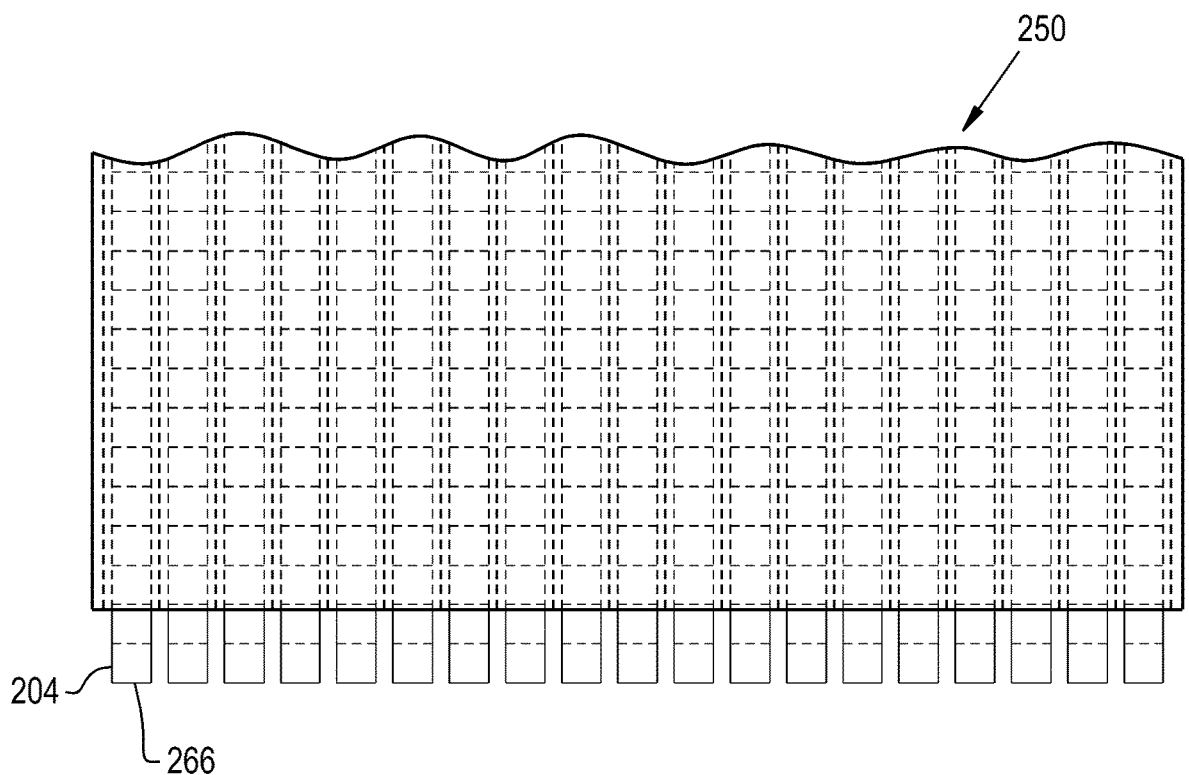
FIG. 21 illustrates the blanket of the present invention with the linear arrays of weighted pockets having been inserted into the channels of the blanket of the present invention.
Figure 22:
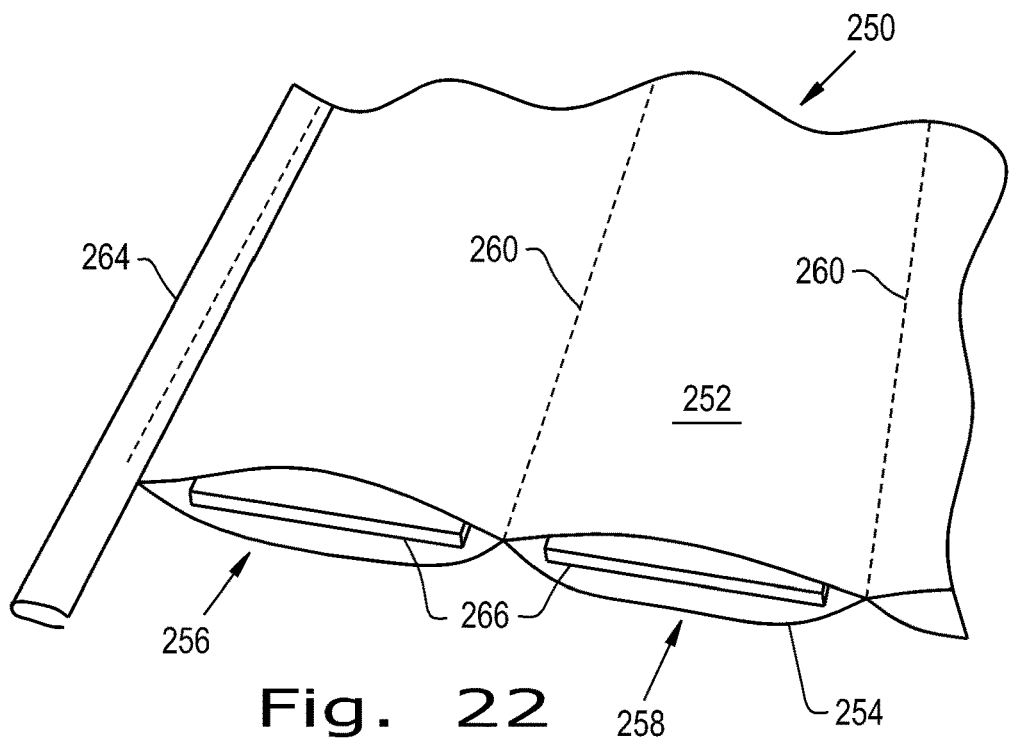
FIG. 22 illustrates a trimmed array and the edges of fabric at an end of an open channel of the blanket illustrated in a previous figure.
Figure 23:
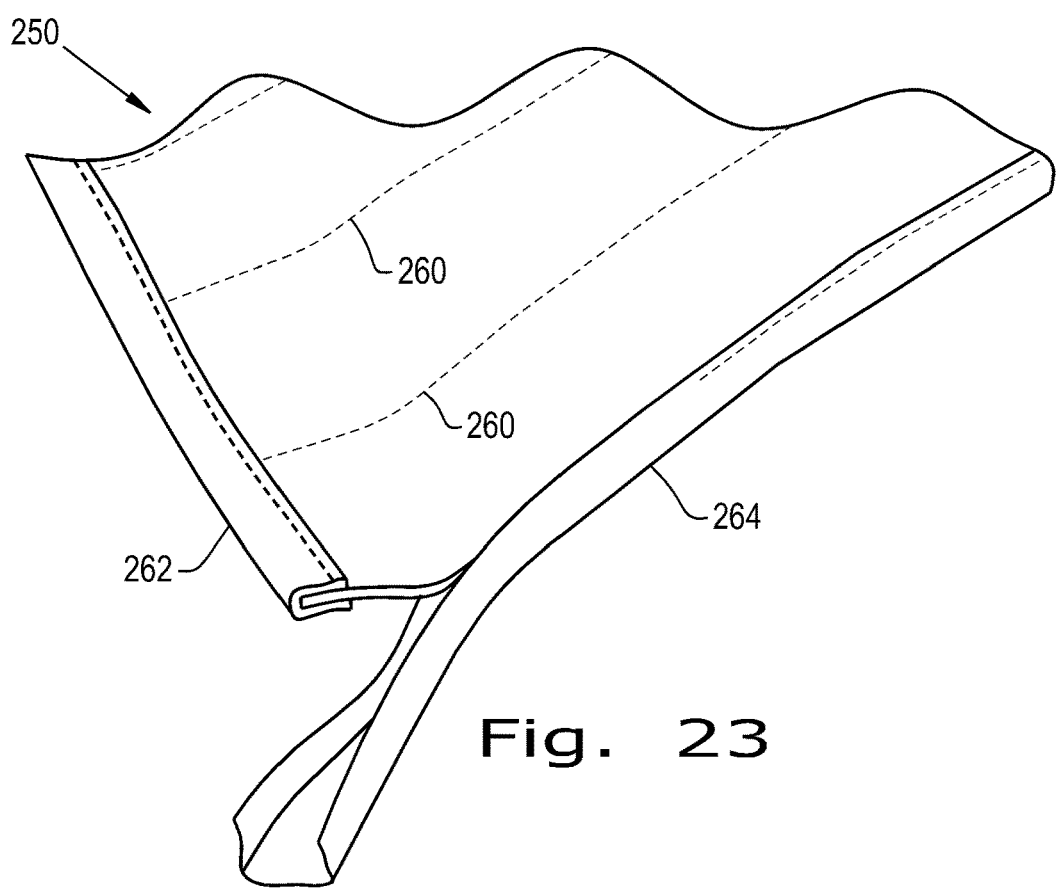
FIG. 23 illustrates the application of edging to the blanket or a garment previously shown.

Now, additionally referring to FIGS. 19-23, there are shown the steps of making blanket 250, as well as the internal structure thereof. Linear arrays 266 of filled elements (weighted sections) 204 are arranged to be pulled into each channel 256/258 using a pulling device 268. Pulling device 268 is a stiffened yet flexible item that is pushed through each channel 256/258 to which each linear array 266 is temporarily coupled and the pulling of device 268 allows each linear array 266 to be positioned in a respective channel, as shown in FIGS. 19 and 20. As shown in FIG. 21 linear arrays 266 have been positioned in each channel of blanket 250, and are arranged so that an end of each linear array 266, as shown in FIG. 22, is positioned at an end of each channel 256/258, so that end piece 262 can be seamed, at each end of channel 256/258, to thereby captivate the ends of each linear array 266 to fabric layers 252 and 254.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:
1. A blanket, comprising:
a first outer layer;
a second outer layer attached to the first outer layer, at least one channel formed between the first outer layer and the second outer layer including a first channel;
at least one linear array of weighted sections including a first linear array of weighted sections, the first linear array of weighted sections being inserted into the first channel and being secured at an end of the first channel;
wherein the blanket is configured as a perimeter blanket, wherein the perimeter blanket includes a perimeter area where the linear array of weighted sections is situated; and
wherein the perimeter blanket further includes a plurality of magnetic inserts in the first linear array of weighted sections, adjacent sections having the magnetic inserts arranged so that alternating magnetic polarities are positioned to a common side of the adjacent sections around at least a portion of a periphery of the perimeter blanket.

2. The blanket of claim 1, wherein the first linear array of weighted sections is secured at both ends of the first channel.

3. The blanket of claim 1, wherein the at least one channel includes a second channel, the at least one linear array of weighted sections including a second linear array of weighted sections, the first channel being parallel with the second channel, the second linear array of weighted sections being inserted into the second channel, the first and second linear arrays of weighted sections being secured at each end to the first outer layer and the second outer layer.

4. The blanket of claim 1, wherein the linear array of weighted sections have a weighted filling in each of the sections.

5. The blanket of claim 4, wherein the weighted filling includes a plurality of glass or polymer pellets in each of the sections.

6. The blanket of claim 5, wherein each of the sections have a substantially equal amount of filling therein.

7. The blanket of claim 6, wherein each of the sections have a generally square shape.

8. The blanket of claim 5, wherein each section of the linear array of weighted sections is configured to be sequentially sealed after a preselected amount of glass or polymer pellets are inserted therein.

9. The blanket of claim 1, wherein at least one of the first layer and the second layer is a plush fabric material with a slight elasticity.

10. A layered fabric item, comprising:
a first outer fabric layer;
a second outer fabric layer attached to the first outer fabric layer, at least one channel formed between the first fabric outer layer and the second fabric outer layer including a first channel;
at least one linear array of weighted sections including a first linear array of weighted sections, the first linear array of weighted sections being inserted into the first channel and being secured at an end of the first channel; and
a plurality of magnetic inserts, the at least one channel including a second channel, the at least one linear array of weighted sections including a second linear array of weighted sections, the first channel being parallel with the second channel, the second linear array of weighted sections being inserted into the second channel, a majority of the weighted sections of the first linear array and the second linear array are weighted with at least one of the magnetic inserts therein, the magnetic inserts in the first linear array of weighted sections being arranged so that adjacent sections have the magnetic inserts arranged so that alternating magnetic polarities are positioned to a common side of the adjacent sections.

11. The layered fabric item of claim 10, wherein the fabric item only has two linear arrays of weighted sections, each of the weighted sections having one of the magnetic inserts therein, each of the magnetic inserts being arranged such that each adjacent magnetic insert has an opposite magnetic polarity facing the first outer fabric layer.

12. The layered fabric item of claim 10, wherein the linear array of weighted sections have a weighted filling in each of the sections, the weighted filling includes a plurality of glass or polymer pellets in each of the sections.

13. The layered fabric item of claim 12, wherein each of the sections have a substantially equal amount of filling therein.

14. The layered fabric item of claim 10, wherein the first linear array of weighted sections is secured at both ends of the first channel and is not directly connected to the first outer fabric layer of the second outer fabric layer other than at the ends of the first channel.

15. The layered fabric item of claim 10, wherein the at least one channel includes a second channel, the at least one linear array of weighted sections including a second linear array of weighted sections, the first channel being parallel with the second channel, the second linear array of weighted sections being inserted into the second channel, the first and second linear arrays of weighted sections being secured at each end to the first fabric outer layer and the second fabric outer layer.

* * * * *